United States Patent [19]

Koshino et al.

[11] Patent Number: 5,049,544
[45] Date of Patent: Sep. 17, 1991

[54] PERFUMERY COMPOSITION COMPRISING 2-CYCLOHEXYLPROPIONIC ACID OR ITS DERIVATIVE

[75] Inventors: Junji Koshino, Naga; Yoshiaki Fujikura, Utsunomiya; Nao Toi, Sakura, all of Japan

[73] Assignee: Kao Corporation, Tokyo, Japan

[21] Appl. No.: 558,504

[22] Filed: Jul. 27, 1990

[30] Foreign Application Priority Data

Jul. 28, 1989 [JP] Japan .................................. 1-195610

[51] Int. Cl.$^5$ ................................................ A61K 7/46
[52] U.S. Cl. ................................................ 512/22
[58] Field of Search .................................... 572/22

[56] References Cited

U.S. PATENT DOCUMENTS

| | | | |
|---|---|---|---|
| 2,710,825 | 6/1955 | Lazier et al. | 512/22 |
| 2,859,239 | 11/1958 | Trapp et al. | 512/22 |
| 4,704,477 | 4/1987 | Gebauer et al. | 512/22 |
| 4,918,052 | 4/1990 | Koshino et al. | 512/22 |

FOREIGN PATENT DOCUMENTS

| | | | |
|---|---|---|---|
| 202553 | 11/1986 | Fed. Rep. of Germany | 512/23 |
| 2378737 | 8/1978 | France | 512/22 |
| 59-204115 | 11/1984 | Japan | 512/22 |
| 326959 | 9/1989 | Japan | 512/23 |

OTHER PUBLICATIONS

J. Chem. Soc., p. 1483 (1933).
Tet. Lett., vol. 22, pp. 1891 (1981).
Ann. N.Y., Acad. Sci., vol. 415, p. 148 (1983).
Chem. Ber., vol. 119, p. 509 (1986).
Tet. Lett., vol. 24, p. 1315 (1983).
Patent Abstracts of Japan vol. 4, No. 124 (1 pg.).
Tetrahedron Letters, vol. 22, No. 20, pp. 1891–1894, 1981.
Tetrahedron Letters, vol. 24, No. 12, pp. 1315–1318, 1983.

*Primary Examiner*—James H. Reamer
*Attorney, Agent, or Firm*—Oblon, Spivak, McClelland, Maier & Neustadt

[57] ABSTRACT

Disclosed is a perfumery composition comprising a 2-cyclohexylpropionic acid or its derivative represented by the following formula (I):

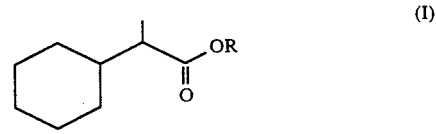

wherein R is a hydrogen atom, an alkyl group having 1–4 carbon atoms, or an alkenyl group having 2–4 carbon atoms.

The compounds have a wide variety of odors and a wide application as perfumery compositions such as high-grade perfumery compositions, perfumes, soaps, shampoos, rinses, detergents, cosmetics, sprays, room fragrances, and the like.

7 Claims, No Drawings

PERFUMERY COMPOSITION COMPRISING 2-CYCLOHEXYLPROPIONIC ACID OR ITS DERIVATIVE

BACKGROUND OF THE INVENTION

1. Field of the Invention

The present invention relates to a perfumery composition comprising 2-cyclohexylpropionic acid or its derivative.

2. Description of the Background Art

There are many compounds known as possible odorizing substances for perfumery. These perfumery compounds are required to be easy to synthesize, economical, chemically stable, compatible with other ingredients and novel in their odor. It is, therefore, very important to examine the possibility of various compounds for use as a fragrance-imparting agent.

In view of the fact that carboxylic acids or esters having a cyclohexyl group can readily be synthesized and are appropriate for industrial application, the present inventors have conducted extensive studies on their aromaticity and their applicability as a fragrance-imparting agent.

As a result, the inventors have found that 2-cyclohexylpropionic acid or its derivatives can provide various kinds of odors when incorporated as a perfume ingredient in perfumery compositions. Such a finding has led to the completion of the present invention.

SUMMARY OF THE INVENTION

Accordingly, an object of this invention is to provide a perfumery composition comprising a 2-cyclohexylpropionic acid or its derivative represented by the following formula (I):

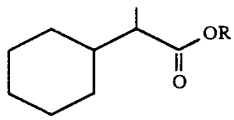
(I)

wherein R is a hydrogen atom, an alkyl group having 1-4 carbon atoms, or an alkenyl group having 2-4 carbon atoms.

Other objects, features and advantages of the invention will hereinafter become more readily apparent from the following description.

DETAILED DESCRIPTION OF THE INVENTION AND PREFERRED EMBODIMENTS

2-Cyclohexylpropionic acid and its derivatives of formula (I) are known compounds. Processes for synthesizing these compounds have been disclosed in the art. Included as these compounds are 2-cyclohexylpropionic acid disclosed in *J. Chem. Soc.*, 1483, (1933); methyl 2-cyclohexylpropionate disclosed in *Tetrahedron Lett.*, 22, 1891, (1981), *Ann. N. Y. Acad. Sci.*, 415, 148, (1983), *Chem. Ber.*, 119, 509, (1986), etc.; ethyl 2-cyclohexylpropionate disclosed in *Tetrahedron Lett.*, 24, 1315, (1983) etc.; and tert-butyl 2-hexylpropionate disclosed in *Organometallics*, 2, 363, (1983). However, the aromaticity or benefit of these compounds as a fragrance-imparting agent have never been reported in the above publications.

The compounds of formula (I) used in the perfumery compositions of the present invention can be prepared according to the processes described in the above publications or by either of the following processes (A)–(E):

Process (A)

2-Phenylpropionate is hydrogenated according to the following reaction scheme to obtain 2-cyclohexylpropionate.

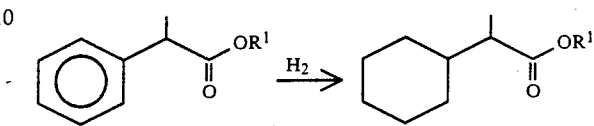

wherein $R^1$ is an alkyl group having 1-4 carbon atoms.

It is desirable that this reaction be carried out using 0.001–0.1 equivalent of Raney nickel, platinum, palladium, ruthenium or rhodium catalyst under a hydrogen pressure of 10–200 atm at a temperature of 80°–200° C.

Process (B)

2-Cyclohexylpropionate is hydrolyzed according to the following reaction scheme to obtain 2-cyclohexylpropionic acid.

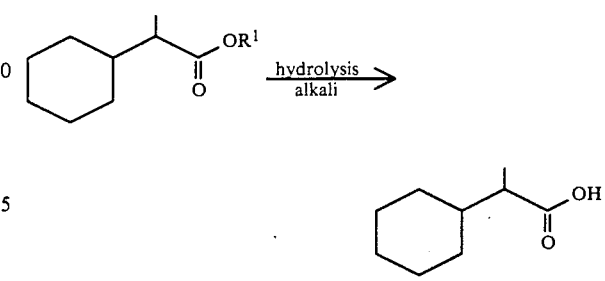

wherein $R^1$ has the same meaning as defined above.

It is desirable that this reaction be carried out using aqueous sodium hydroxide, potassium hydroxide, or the like as an alkali at a temperature of 20°–100° C. to produce a salt of carboxylic acid, followed by neutralization with sulfuric acid or other mineral acid.

Process (C)

2-Cyclohexylpropanal is oxidized using air or oxygen according to the following reaction scheme to produce 2-cyclohexylpropionic acid.

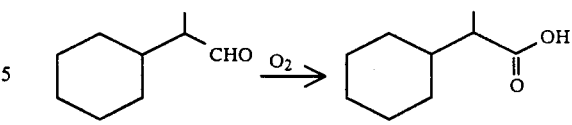

It is preferable that this reaction be carried out by blowing air or oxygen into 2-cyclohexylpropanal in the absence or presence of a metal catalyst, e.g. cobalt, manganese, nickel, chromium, copper, vanadium, as required, at 20°–100° C. without any solvent.

Process (D)

2-Cyclopropionic acid is reacted with an alcohol in the presence of an acid catalyst according to the following reaction scheme to obtain 2-cyclohexylpropionate.

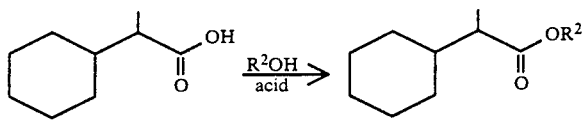

wherein $R^2$ is an alkyl group having 1–4 carbon atoms or an alkenyl group having 2–4 carbon atoms.

It is desirable that this reaction be carried out by azeotropic dehydration using 1–10 equivalent of an alcohol; 0.001–0.1 equivalent of sulfuric acid, p-toluene sulfonic acid, or the like as an acid catalyst; and dichloromethane, chloroform, or the like as a reaction solvent.

Process (E)

2-Cyclohexylpropionic acid is reacted with isobutene in the presence of an acid catalyst according to the following reaction scheme to obtain tert-butyl 2-cyclohexylpropionate.

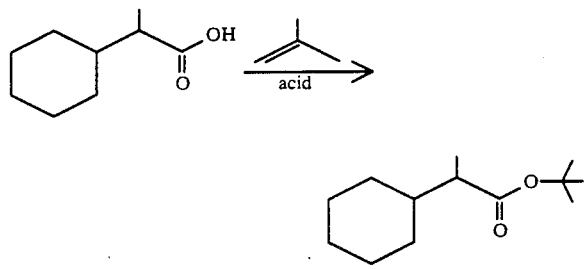

It is desirable that this reaction be carried out at a temperature of 0°–30° C. using 1–10 equivalent of isobutene; 0.001–0.1 equivalent of sulfuric acid, boron trifluoride diethyl ether, or the like as an acid catalyst; and ether as a reaction solvent.

The compound (I) is incorporated in the perfumery composition of the present invention without any limitations as to the amount, but preferably in an amount of 0.1–50% by weight, particularly preferably of 5–40% by weight.

By using the compounds (I) of the present invention as a fragrance-imparting agent in an admixture with conventional fragrance-imparting agents and a carrier thereof, various odors are imparted to perfumery compositions. The compounds can be used in a wide variety of products which require pleasant odors or fragrances such as high-grade perfumery compositions, perfumes, soaps, shampoos, rinses, detergents, cosmetics, sprays, room fragrances, and the like.

Other features of the invention will become apparent in the course of the following description of the exemplary embodiments which are given for illustration of the invention and are not intended to be limiting thereof.

EXAMPLES

Preparation Example 1

Synthesis of methyl 2-cyclohexylpropionate

Into a 100 ml autoclave 50 g of methyl 2-phenylpropionate, 0.5 g of ruthenium catalyst on 5% activated carbon as a carrier (manufactured by Nippon Engerhard Co.) were charged. The mixture was reacted under a hydrogen pressure of 50 Kg/cm² at 150° C. for 8 hours. After completion of the reaction, the catalyst was removed by filtration to obtain 50.5 g of a product.

The product was analyzed by means of gas chromatography and confirmed that methyl 2-cyclohexyl-propionate of 99% purity was formed (yield: 97%). The compound obtained had a grassy, drygrassy, and woody odor.

Boiling Point: 70° C. at 5 mmHg

IR (liquid film, cm$^{-1}$): 2932, 2854, 1743, 1455, 1197, 1167, 1149

NMR (CDCl$_3$, TMS internal standard, δ ppm):
1.08(d, J=7Hz, 3H), 1.2–2.0(m, 11H), 2.15(m, 1H), 3.60(s, 3H)

GC-MS(M+): 170

Preparation Example 2

Synthesis of 2-cyclohexylpropionic acid

Into a 500 ml round bottom flask 50 g of methyl 2-cyclohexylpropionate and 70 g of 25% sodium hydroxide were charged. The mixture was stirred at 80° C. for 8 hours. To the reaction mixture 120 g of 20% sulfuric acid was gradually added under ice-cooling to separate a carboxylic acid. The carboxylic acid was extracted with hexane. The mixture obtained was distilled to obtain 42.3 g of 2-cyclohexylpropionic acid having a civet- and animal-like odor (yield: 92%, purity: 99.9%).

Boiling Point: 114° C. at 2 mmHg

IR (KBr tablet, cm$^{-1}$): 3600–2400, 2920, 2848, 2662, 1701, 1290, 1245, 1209, 940

NMR (CDCl$_3$, TMS internal standard, δ ppm):
1.13(d, J=7Hz, 3H), 1.2–2.0(m, 11H), 2.23(m, 1H)

Preparation Example 3

Synthesis of 2-cyclohexylpropionic acid

Into a 500 ml round bottom flask was charged 300 g of 2-cyclohexylpropanal and was fed a stream of oxygen at a rate of 100 ml per minute at 60° C. for 80 hours through a sintered liquid filter for liquid chromatography. The reaction mixture was analyzed by means of gas chromatography and confirmed that 2-cyclohexylpropionic acid was obtained in an yield of 65% and 35% of the 2-cyclohexylpropanal remained unreacted in the reaction mixture.

Preparation Example 4

Synthesis of ethyl 2-cyclohexylpropionate

Into a 500 ml round bottom flask equipped with a Soxhlet extractor filled with molecular sieves, 50 g of 2-cyclo-hexylpropionate, 100 g of ethanol, 0.5 g of p-toluene sulfonic acid, and 200 ml of chloroform were charged. The mixture was reacted under refluxing for 40 hours. The reaction mixture was washed with water and distilled under reduced pressure to obtain 56.4 g of ethyl 2-cyclohexylpropionate (yield: 96%, purity: 99.4%). The compound obtained had a fruity (namely aldehyde C-16 and apple-like) odor.

Boiling Point: 80° C. at 5 mmHg

IR (Liquid film, cm$^{-1}$): 2980, 2932, 2854, 1737, 1191, 1173, 1149

NMR (CDCl$_3$, TMS internal standard, δ ppm):
1.08(d, J=7Hz, 3H), 1.25(t, J=7Hz, 3H), 1.2–2.0(m, 11H), 2.18(m, 1H), 4.13(q, J=7Hz, 2H)

GC-MS(M+): 184

Preparation Example 5

Synthesis of isopropyl 2-cyclohexylpropionate

Isopropyl 2-cyclohexylpropionate was prepared in the same manner as in Preparation Example 4 in an yield of 80%, except that instead of ethanol 100 g of isopropanol was used. The compound obtained had a floral, woody, and fruity odor.

Boiling Point: 90.5° C. at 5 mmHg
IR (Liquid film, cm$^{-1}$): 2980, 2932, 2854, 1734, 1194, 1176, 1149, 1110
NMR (CDCl$_3$, TMS internal standard, δ ppm):
1.08(d, J=7Hz, 3H), 1.24(d, J=7Hz, 6H), 1.2–2.0(m, 11H), 2.15(m, 1H), 5.03(sep, J=7Hz, 1H)
GC-MS(M+): 198

Preparation Example 6

Synthesis of allyl 2-cyclohexylpropionate

Allyl 2-cyclohexylpropionate was prepared in the same manner as in Preparation Example 4 in an yield of 67%, except that instead of ethanol 100 g of allyl alcohol was used. The compound obtained had a fruity and allylic odor.

Boiling Point: 85° C. at 5 mmHg
IR (Liquid film, cm$^{-1}$): 3140, 2932, 2854, 1737, 1170, 1146
NMR (CDCl$_3$, TMS internal standard, δ ppm):
1.13(d, J=7Hz, 3H), 1.2–2.0(m, 11H), 2.23(m, 1H), 4.54(d, J=6Hz, 2H), 5.20(br. d, J=9Hz, 1H), 5.38(br. s, 1H), 5.5–6.3(m, 1H)
GC-MS(M+): 196

Preparation Example 7

Synthesis of tert-butyl 2-cyclohexylpropionate

Into a 500 ml round bottom flask 30 g of 2-cyclohexylpropionic acid and 200 ml of ether were charged and cooled to 0° C. After 100 g of isobutene gas was introduced, 0.5 g of sulfuric acid was charged into the mixture, the mixture was then stirred at 0° C. for 40 hours. The reaction mixture was washed with water and distilled under reduced pressure to obtain 4.5 g of tert-butyl 2-cyclohexylpropionate having a woody and floral odor (yield: 11%, purity: 98.7%).

Boiling Point: 80° C. at 5 mmHg
IR (Liquid film, cm$^{-1}$): 2974, 2932, 2854, 1731, 1146
NMR (CDCl$_3$, TMS internal standard, δ ppm):
1.08(d, J=7Hz, 3H), 1.2–2.0(m, 11H), 1.50(s, 9H), 2.15(m, 1H)
GC-MS(M+): 212

Example 1

Apple-type Perfumery Composition

| | |
|---|---|
| 2-Methylbutyl n-butylate | 20 parts by weight |
| Cis-3-hexenol | 5 |
| Cis-3-hexenyl acetate | 5 |
| Ligustral *1 | 10 |
| 2-Cyclohexylpropanal | 20 |
| δ-decalactone | 10 |
| Fruitate *2 | 50 |
| Geranial n-butylate | 100 |
| Diethyl malonate | 100 |
| α-Damascone | 20 |
| Sagetone V *3 | 200 |
| Nerolidol | 60 |
| | 600 |

*1: 2,4-dimethyl-3-cyclohexene-1-carboxyaldehyde, Specialty Chemical manufactured by Quest Inc.
*2: Ethyltricyclo[5.2.1.0$^{2,6}$]decane 2-carboxylate, Specialty Chemical manufactured by Kao Corporation.
*3: Spiro[bornane-3,1'-cyclopenta-2-one], Specialty Chemical manufactured by Kao Corporation.

An apple-type perfume was prepared by blending 600 parts by weight of the above components and 400 parts by weight of ethyl 2-cyclohexylpropionate. The perfume possessed a fresh and fruity odor.

Example 2

A natural, fresh and green-floral perfume was prepared by using methyl 2-cyclohexylpropionate as a fragrance-imparting agent.

Example 3

A citrus-floral perfume with an intensified natural scent was prepared by using 2-cyclohexylpropionic acid as a fragrance-imparting agent.

Example 4

A fruity-floral perfume was prepared by using isopropyl 2-cyclohexylpropionate as a perfume substance.

Example 5

A pineapple-like, fruity-floral perfume was prepared by using allyl 2-cyclohexylpropionate as a perfume substance.

Example 6

A soft and floral perfume was prepared by using tert-butyl 2-cyclohexylpropionate as a perfume substance.

Obviously, numerous modifications and variations of the present invention are possible in light of the above teachings. It is therefore to be understood that within the scope of the appended claims, the invention may be practiced otherwise than as specifically described herein.

What is claimed is:

1. A perfumery composition comprising a 2-cyclohexylpropionic acid or its derivative represented by the following formula (I):

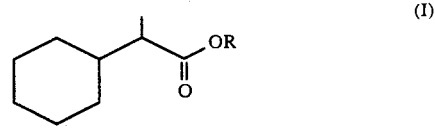

wherein R is a hydrogen atom, an alkyl group having 1–4 carbon atoms, or an alkenyl group having 2–4 carbon atoms, in a mixture with conventional components of a perfumery composition.

2. The composition of claim 1 comprising ethyl 2-cyclohexylpropionate.

3. The composition of claim 1 comprising methyl 2-cyclohexylpropionate.

4. The composition of claim 1 comprising 2-cyclohexylpropionic acid.

5. The composition of claim 1 comprising isopropyl 2-cyclohexylpropionate.

6. The composition of claim 1 comprising allyl 2-cyclohexylpropionate.

7. The composition of claim 1 comprising tert-butyl 2-cyclohexylpropionate.

* * * * *